US008771209B2

(12) United States Patent
Evans

(10) Patent No.: US 8,771,209 B2
(45) Date of Patent: Jul. 8, 2014

(54) KNITTED SUBSTRATE FOR USE IN MEDICAL BANDAGING PRODUCT AND BANDAGING PRODUCT

(71) Applicant: BSN Medical, Inc., Charlotte, NC (US)

(72) Inventor: John C. Evans, Nr Rochdale (GB)

(73) Assignee: BSN Medical, Inc., Charlotte, NC (US)

( * ) Notice: Subject to any disclaimer, the term of this patent is extended or adjusted under 35 U.S.C. 154(b) by 0 days.

(21) Appl. No.: 13/711,003

(22) Filed: Dec. 11, 2012

(65) Prior Publication Data
US 2013/0146493 A1 Jun. 13, 2013

Related U.S. Application Data

(60) Provisional application No. 61/569,520, filed on Dec. 12, 2011.

(51) Int. Cl.
*A61F 5/00* (2006.01)
(52) U.S. Cl.
USPC .................. 602/6; 602/1; 602/5; 206/440
(58) Field of Classification Search
USPC ................ 602/44, 43, 6–8; 206/440
See application file for complete search history.

(56) References Cited

U.S. PATENT DOCUMENTS

| 3,900,024 | A | 8/1975 | Lauber et al. |
| 3,923,049 | A | 12/1975 | Lauber et al. |
| 4,235,228 | A | 11/1980 | Gaylord, Jr. et al. |
| 4,267,709 | A * | 5/1981 | Hittel ............................... 66/87 |
| 4,411,262 | A | 10/1983 | von Bonin et al. |
| 4,502,479 | A | 3/1985 | Garwood et al. |
| 4,770,299 | A | 9/1988 | Parker |
| 5,003,970 | A | 4/1991 | Parker et al. |
| 7,854,712 | B2 | 12/2010 | Evans et al. |
| 7,960,603 | B2 | 6/2011 | Evans |
| 7,972,288 | B2 | 7/2011 | Chabba et al. |
| 2004/0193083 | A1 * | 9/2004 | Evans et al. ...................... 602/8 |

* cited by examiner

Primary Examiner — Anthony Stashick
Assistant Examiner — James Way
(74) Attorney, Agent, or Firm — Shumaker, Loop & Kendrick, LLP

(57) ABSTRACT

A medical bandaging product including a sealable enclosure and a resin-impregnated substrate including a knitted fabric layer having upper and lower surfaces with interconnected knitted fabric yarns knitted such that at least one yarn extends across a gap from the upper surface to the lower surface along a width of the substrate in a back-and-forth pattern forming a single, integrated three-dimensional structure, wherein the at least one yarn extends between non-adjacent needle positions in a back-and-forth pattern in successive courses to provide a continuous pattern on both the upper and lower major surfaces of the substrate, wherein needle bed gap spacing is between 7.1 mm and 8 mm and a total thickness of the substrate is between 4.75 mm and 4.90 mm.

14 Claims, 7 Drawing Sheets

KNITTED SUBSTRATE FOR USE IN MEDICAL BANDAGING PRODUCT AND BANDAGING PRODUCT

CROSS-REFERENCE TO RELATED APPLICATION

This U.S. non-provisional application claims the benefit of U.S. Provisional Application No. 61/569,520 filed Dec. 12, 2011, the entirety of which is incorporated by reference herein.

TECHNICAL FIELD AND BACKGROUND OF THE INVENTION

This invention relates generally to the field of orthopedic medicine, and more particularly, to a medical bandaging product and material that includes a warp knitted, double-layered fabric substrate. The substrate material disclosed herein achieves enhanced strength as a result of novel structural characteristics not found in the prior art.

Medical bandages for use in the treatment of injuries, such as broken bones requiring immobilization of a body member, are generally formed from a strip of fabric or scrim material impregnated with a substance that hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like, and then over-wrapping the covering and limb with a woven cloth impregnated with plaster-of-paris that has been wetted by dipping in water immediately prior to application. This practice is still in widespread use, but possesses several significant disadvantages. For example, the above-described application procedure is messy, time consuming, requires several components, and requires considerable skill.

In order to alleviate the above-recited disadvantages of the conventional application procedure for plaster-of-paris casts and splints, unitary splinting materials have been devised and are disclosed in, for example, U.S. Pat. No. 3,900,024, U.S. Pat. No. 3,923,049, and U.S. Pat. No. 4,235,228. All of these patents describe a padding material with a plurality of layers of plaster-of-paris impregnated cloth.

A significant advance in the art of casting and splinting is disclosed in U.S. Pat. No. 4,411,262 and U.S. Pat. No. 4,502,479. The casting materials disclosed in these patents include bandaging materials that incorporate a substrate formed from a plurality of flexible fabric layers, such as fiberglass, impregnated with a moisture-curing resin. These bandaging materials are enclosed in a moisture-free, moisture-impervious package until use. Compared to plaster-of-paris, these products are extremely lightweight, have a very high strength-to-weight ratio and can be made relatively porous, permitting a flow of air through the casting material. However, no provision has been made for moisture-curing systems that incorporate a substrate that is formed from a single layer of fabric, yet is strong and absorbent enough to be impregnated with amounts of moisture-curing resin comparable to those amounts absorbed by conventional multi-layered substrates.

U.S. Pat. No. 4,770,299 and U.S. Pat. No. 5,003,970, among others owned by the present applicant, each disclose roll-form synthetic bandaging products that include the ability to dispense desired lengths of bandaging material when needed, while sealing the remaining length of material for later use. Similar products are also sold in precut lengths sealed in a single use, moisture-impervious envelope.

Both the conventional plaster-of-paris cast and splint products, and the more recent moisture-curable resin cast and splint products possess certain disadvantages. Plaster-of-paris casts are bulky, heavy and difficult to apply. Even though moisture-curable resin bandage products are lightweight, durable and relatively easy to apply, such products remain relatively expensive to produce due to the need to carefully assemble multiple layers of fabric into a long stack of precisely-aligned layers.

This invention combines the advantages of both plaster-of-paris and moisture-curable resin systems while avoiding their respective disadvantages. Unlike prior art resin systems that employ multiple layers of resin-impregnated substrate layers, the resin system of the present invention takes advantage of a single layer of warp-knitted fabric. Substrates of the general type described in this application are known, and are disclosed in, for example, applicant's own issued U.S. Pat. No. 7,972,288, U.S. Pat. No. 7,960,603 and U.S. Pat. No. 7,854,712. This unique substrate fabric employs a continuous inlaid stitch. This results in a double-knitted fabric that has a lighter weight, yet retains the absorption capabilities of multi-layered substrates. Using a single layer of double-knitted fabric in the substrate further results in reduced production and labor costs in comparison with other synthetic cast products. For example, assembly of prior art, multi-layered substrates requires placement of the overlying fabric layers of the substrate by hand, which is a time consuming process. To ensure that the fabric layers do not separate, the layers must then be stitched together by running one or more seams along the entire length of the substrate. Use of a substrate having only one layer eliminates these labor-intensive layering and stitching steps, and results in a bandaging product that is more cost effective to produce.

Eliminating the multi-layered substrate structure also eliminates the rough, uneven edges present on prior art cured substrates. Such frayed edges are commonplace in prior art bandaging products having multi-layered substrates, and materialize after the resin in such substrates undergoes final curing. These rough edges cause irritation and damage to the skin of the patient upon whom the bandage is ultimately applied. In contrast, the substrate of the present invention has uniform side edges that result from using the single-layer of double-knitted fabric, rather than multiple, uneven fabric layers. This novel structure results in a medical bandage product having a moisture-curable substrate that is lighter in weight than conventional products, yet is stronger and more cost-effective to produce. Careful construction and a unique and counterintuitive relationship between the technical inner and outer surfaces and the space between the technical surfaces provide further enhancement in the quality of the substrate, both in comfort, ease of application and ultimate rigidity. More rapid hardening of the substrate provides a more realistic subjective impression of rigidity more in keeping with hardening rated in prior art fiberglass splinting and casting products.

BRIEF SUMMARY OF THE INVENTION

In one aspect, disclosed herein are embodiments of medical bandaging products and substrates for use in medical bandaging products.

In another aspect, disclosed herein is a medical bandaging product including a substrate formed from a single layer of double-knitted fabric capable of absorbing an increased amount of a moisture-curable resin that hardens the substrate upon exposure to moisture to form a rigid, self-supporting structure.

To achieve the foregoing and other aspects, disclosed herein is a substrate including a knitted fabric layer having a major upper surface and an opposing major lower surface (i.e., a "top" and a "bottom"), the knitted fabric layer including spaced apart edges and a plurality of interconnected knitted fabric yarns knitted such that at least one yarn extends across a gap from the major upper surface to the major lower surface along a width of the substrate in a back-and-forth pattern across the gap between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate.

In a further embodiment, the gap spacing may be between 7.1 mm and 8 mm.

In a further embodiment, the total thickness of the substrate may be between 4.75 mm and 4.90 mm.

In a further embodiment, a reactive system may be impregnated into or coated onto the substrate that remains stable when maintained in substantially moisture-free conditions and hardens upon exposure to moisture to cooperate with the three-dimensional structure to form a rigid, self-supporting structure.

In a further embodiment, a soft, flexible wrapping encloses the substrate along its length and provides cushioning between the substrate and the patient.

In a further embodiment, a medical bandaging product is disclosed herein including an enclosure formed of a moisture-impervious material sealable to prevent entry of moisture, and a medical bandage material positioned in the enclosure and sealed therein against entry of moisture until use.

The medical bandage material may include a substrate including a knitted fabric layer having a major upper surface and a major lower surface, the knitted fabric layer including spaced apart edges and a plurality of interconnected knitted fabric yarns knitted such that at least one yarn extends across a gap from the major upper surface to the major lower surface along a width of the substrate in a back-and-forth pattern across the gap between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate, the gap spacing being between 7.1 mm and 8 mm and the total thickness of the substrate being between 4.75 mm and 4.90 mm.

A reactive system may be impregnated into or coated onto the substrate that remains stable when maintained in substantially moisture-free conditions and hardens upon exposure to moisture to cooperate with the three-dimensional structure to form a rigid, self-supporting structure.

The substrate may be enclosed in a cushioning wrapping.

The medical bandaging product may have a length suitable for a given medical use. The medical bandaging product may include an enclosure formed of a moisture-impervious material sealable to prevent entry of moisture. The medical bandage material is positioned in the enclosure and sealed therein against entry of moisture until use.

In a further embodiment, disclosed herein is a medical bandaging product provided in roll form for being dispensed in predetermined lengths suitable for a given medical use. The medical bandaging product includes an elongate sleeve formed of moisture-impervious material and sealable to prevent entry of moisture. An elongate medical bandage material substantially the same length as the sleeve is positioned in the sleeve in a single length along the length of the sleeve and sealed therein against entry of moisture until use. The medical bandage material includes a substrate formed from a single integrated knitted fabric sheet having plurality of interconnected knitted fabric layers forming a three-dimensional structure. A reactive system is impregnated into or coated onto the substrate. The reactive system remains stable when maintained in substantially moisture-free conditions and hardens upon exposure to sufficient moisture to cooperate with the three-dimensional structure to form a rigid, self-supporting structure. A soft, flexible protective wrapping encloses the substrate along its length for providing a cushioning barrier interposed between the substrate and a patient when the medical bandage material is in use. The medical bandage material is positioned in the enclosure for being dispensed in a desired use length from the sleeve, and the sleeve is adapted for being resealed to prevent moisture from entering the enclosure. The gap between the inner and outer surfaces is increased over prior art products, counter intuitively providing more rapid hardening due to an increased rate of water penetration into the thickness of the substrate.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION OF THE INVENTION

Figure 1:
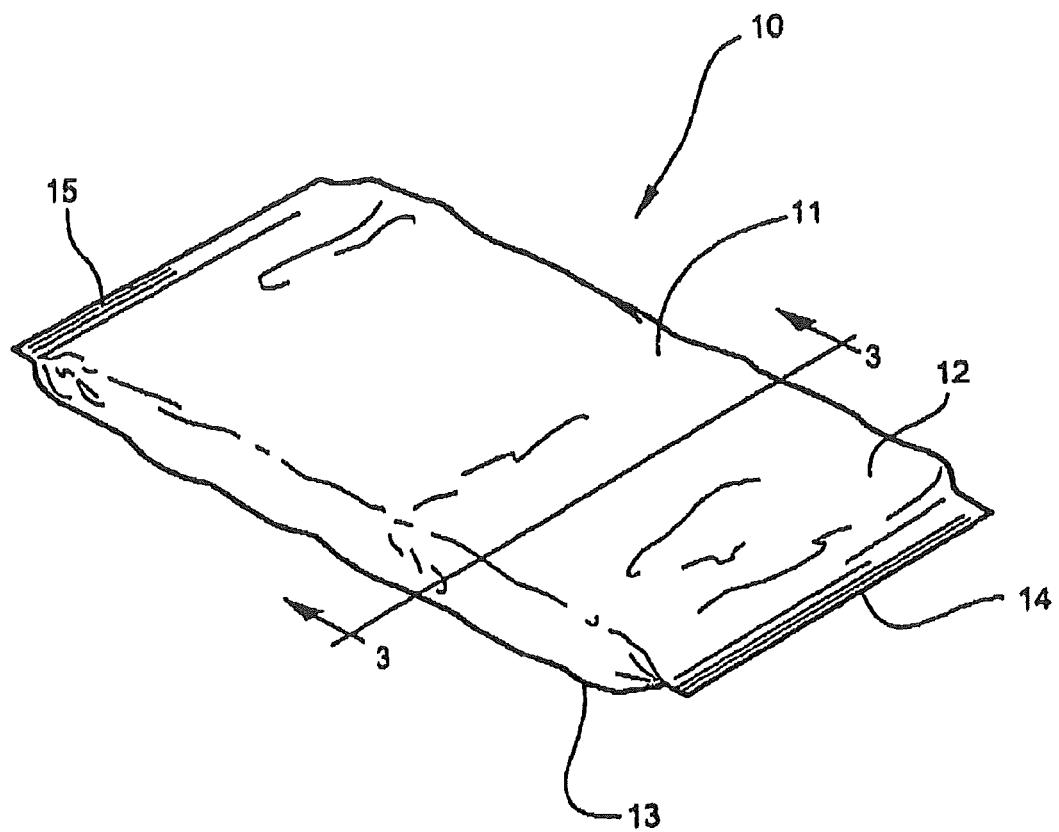
FIG. 1 is a perspective view of a medical bandaging product according to an embodiment of the invention.
Figure 2:
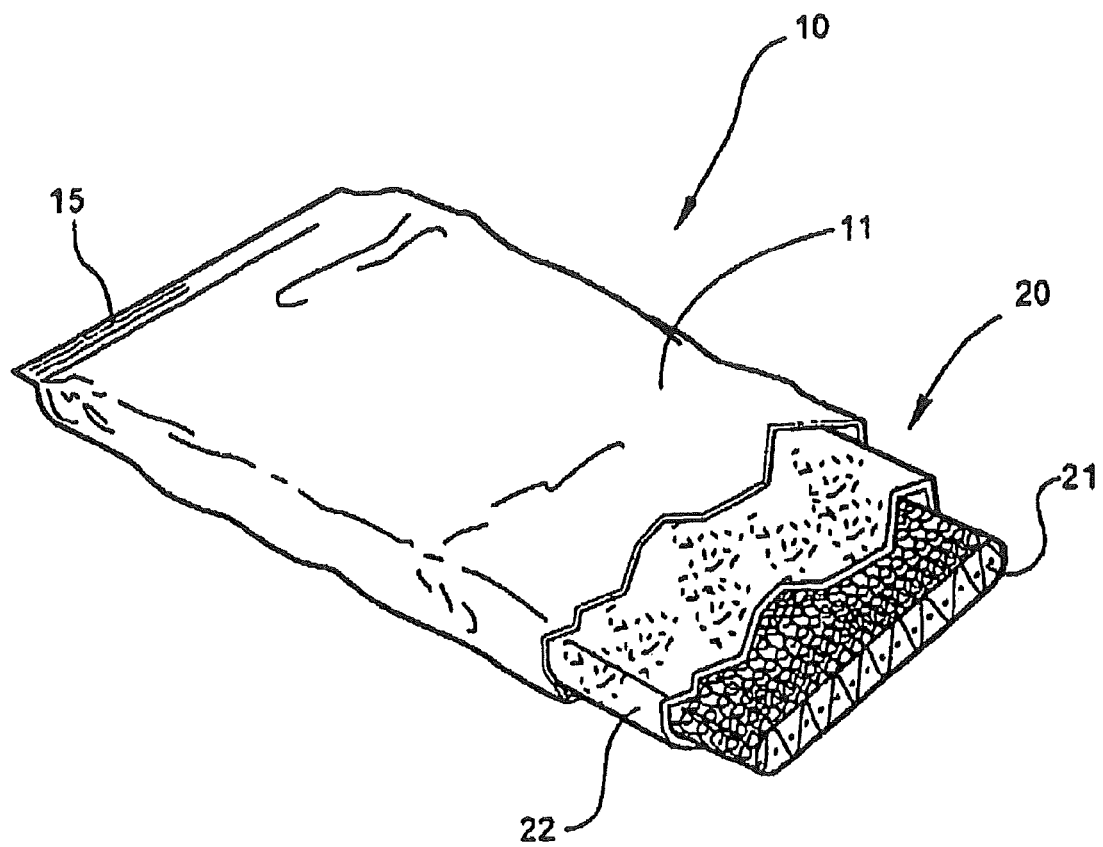
FIG. 2 is a cut-away fragmentary perspective view of the medical bandaging product shown in FIG. 1.
Figure 3:
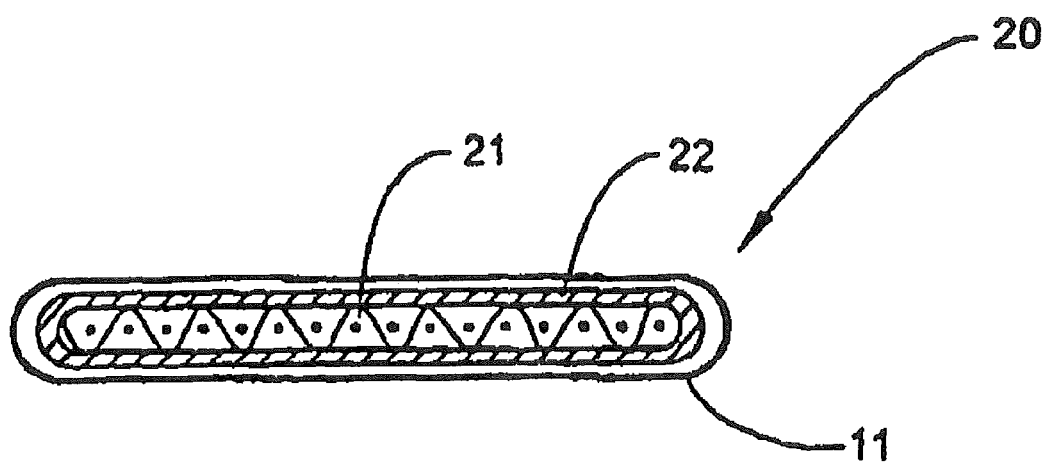
FIG. 3 is a cross-sectional view taken along lines 3-3 of FIG. 1.

Referring now specifically to the drawings, a medical bandaging product according to the present invention is shown generally in FIG. 1 at reference numeral 10. The medical bandaging product 10 includes a moisture-impervious package 11 formed from two laminated sheets 12, 13 that are placed in registration and heat sealed along opposite edges 14 and 15. As is shown in FIGS. 2 and 3, the bandaging product 10 also includes a medical bandage 20 that is maintained in moisture-free conditions within the package 11 until use.

The medical bandage 20 is a "pre-cut" type bandage sized to be used on a pre-determined size and type of body part. The bandage 20 includes a substrate 21 that is encased within an outer cushioned wrapping or cover 22 formed of a soft, flexible, non-woven fiber such as polypropylene or any other suitable hydrophobic fiber. Enclosing the substrate 21 within the cover 22 provides a cushioning protective layer between the skin of a patient and the substrate 21 after the bandage 20 has been applied. As discussed more fully below, the substrate 21 is formed from a single layer of a knitted, relatively open, fabric, such as fiberglass.

The package 11 includes outer, middle and inner layers. The outer layer is preferably formed of a tear-resistant plastic film. The middle layer is preferably formed from aluminum foil and acts as a moisture resistant barrier for protecting the bandage 20 while stored within the package 11. The inner layer is preferably formed from a plastic film having thermoplastic properties suitable for heat-sealing the interior of the package 11 securely against moisture.

Figure 4:
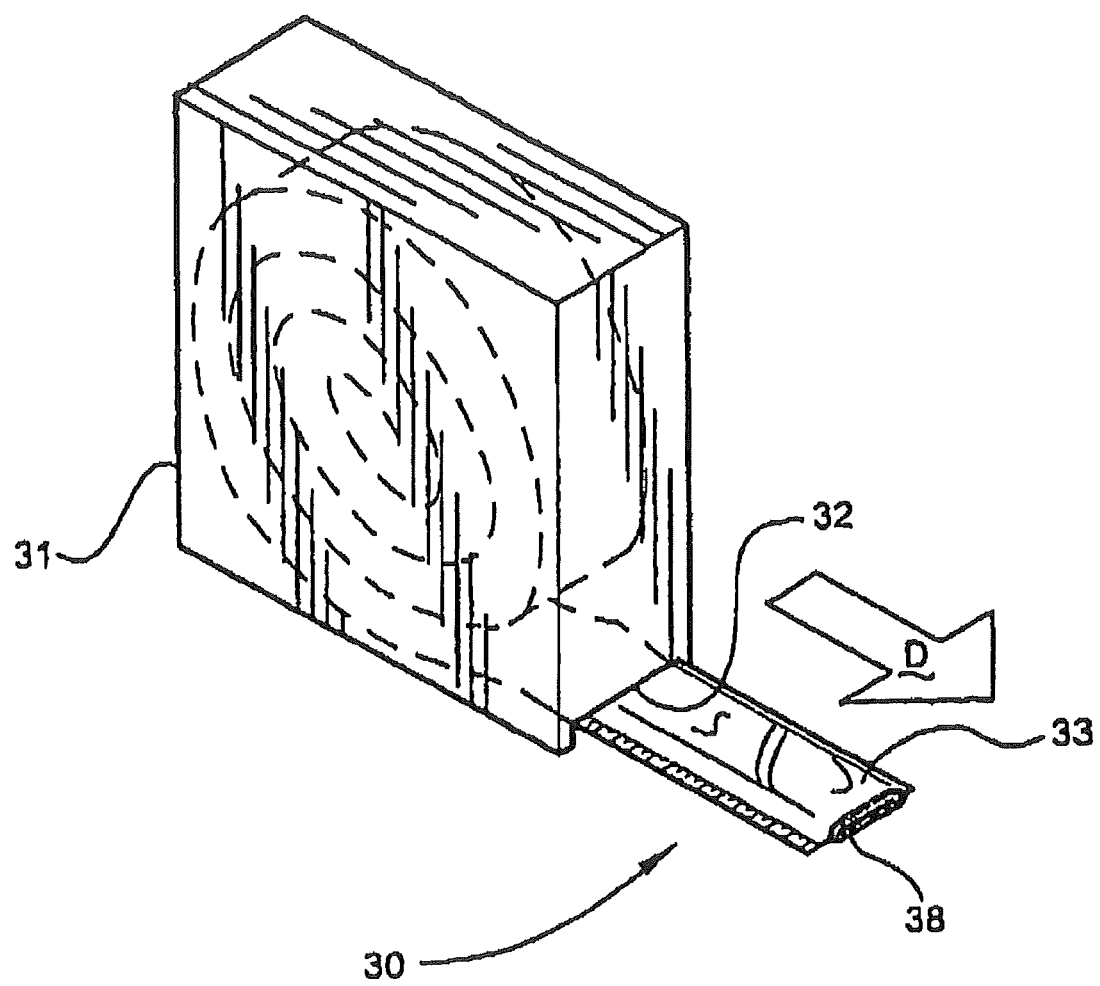
FIG. 4 is a perspective view of a medical bandaging product according to another preferred embodiment of the invention.

Referring now to FIG. 4, a medical bandaging product according to another preferred embodiment of the invention is illustrated and shown generally at reference numeral 30. Bandaging product 30 may be sold in any convenient length, such as 24 feet, and is rolled into a coil and positioned within a suitable dispenser 31. Dispenser 31 is provided with a slot 32 defined in one lower corner through which an end 33 of bandaging product 30 extends for dispensing the product 30 from the dispenser 31 in the direction "D" shown.

Figure 5:
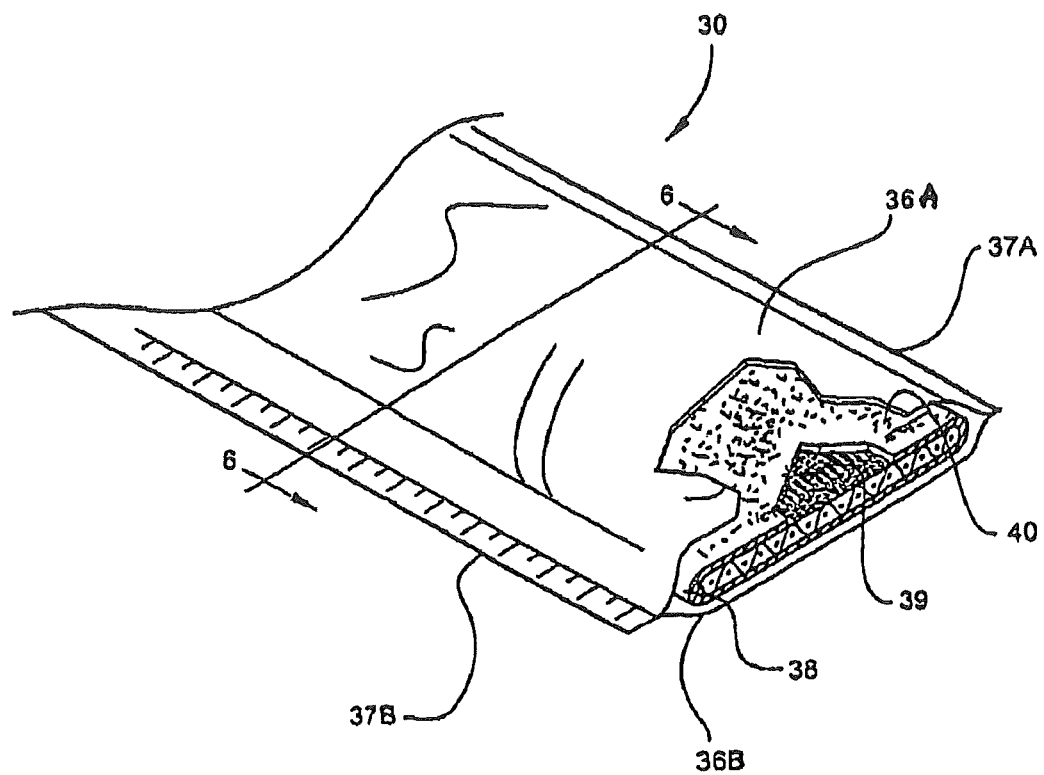
FIG. 5 is a cut-away perspective view of a length of medical bandage material according to FIG. 4.

Referring now to FIG. 5, the bandaging product 30 includes an elongate medical bandaging material 35 that is packaged in moisture-free conditions in a foil sleeve 36. The sleeve 36 is formed from two laminated, elongate foil sheets 36A, 36B, which are placed in registration and heat sealed along opposing side edges 37A, 37B to form a tube having an open end 38. Each sheet 36A and 36B is formed from the same materials and includes the same components as the package 11. The bandage material 35 includes a substrate 39 surrounded by a tubular wrapping 40 formed of the same material as the cover 12 described above in reference to FIG. 3. Enclosing the substrate 39 within the wrapping 40 protects and cushions the skin of a patient from the substrate 39 after the bandage material 35 has been applied.

The substrate 39 is formed from a single layer of a knitted relatively open fabric, such as fiberglass which is identical to that used to form substrate 21. The substrate 21 or 39 may alternatively be formed from polyester.

Figure 6:
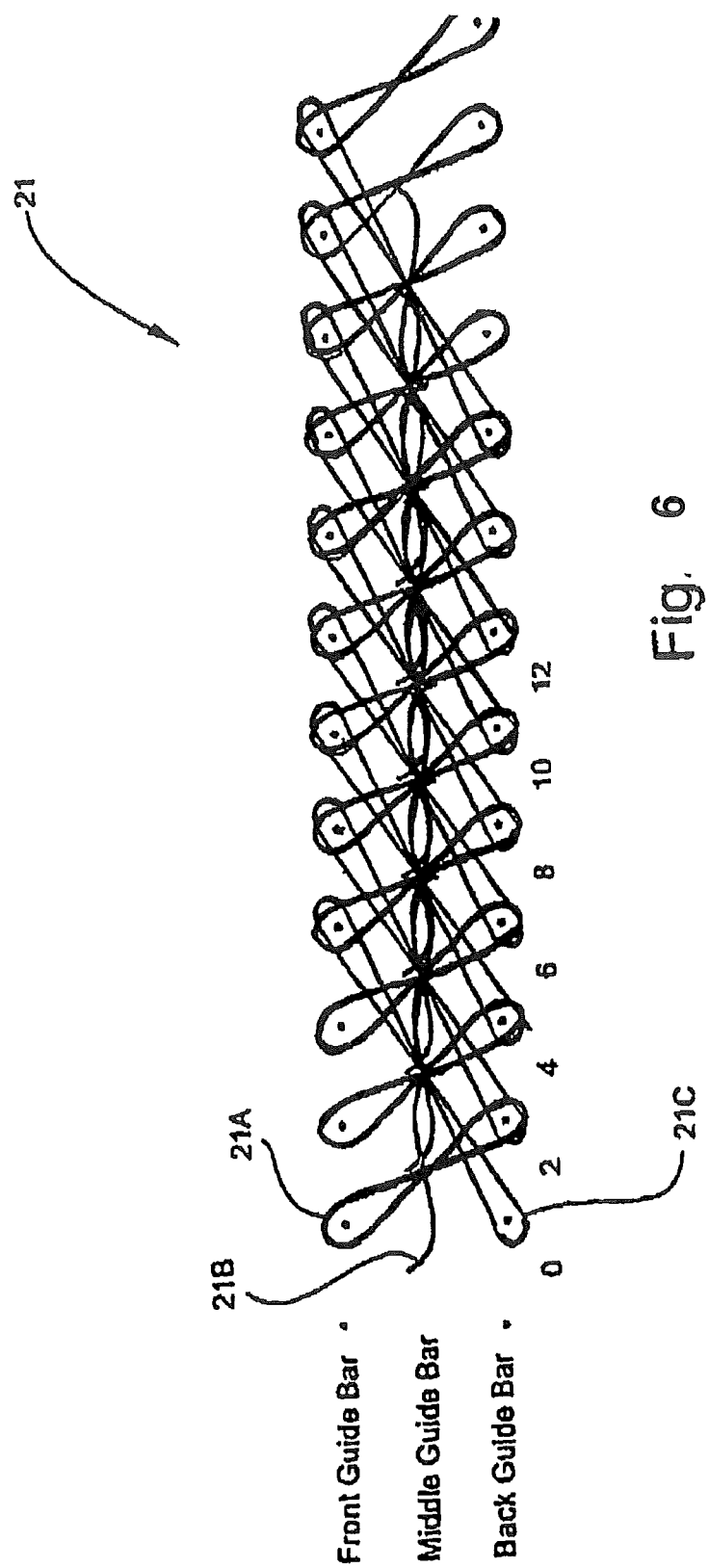
FIG. 6 is a stitch diagram showing the stitch pattern used to form the substrate according to the present invention.

Referring now to FIG. 6, the preferred structure of the fabric used to form both substrate 21 and substrate 39 is shown. The substrate of the present invention is preferably knitted on a warp knitting machine employing three guide bars. These guide bars are shown in the stitch diagram illustrated in FIG. 6 as the front, middle and back guide bars, respectively. Using substrate 21 as a representative example FIG. 6 shows the preferred stitch pattern used to form the substrate 21. Three yarns 21A, 21B, and 21C are employed. Yarn 21A is threaded on the front guide bar and has back-and-forth movement to non-adjacent needles in successive courses as indicated by the numbers (0-2/2-4). Yarns 21B and 21C are threaded on the respective middle and back guide bars and have similar movements as indicated by the numbers (0-0/4-4/8-8/4-4) and (68/0-2) respectively.

Yarns 21A, 21B, and 21C are knitted on the respective front, middle and back guide bars continuously, resulting in a three-dimensional fabric having sufficient weight to absorb adequate quantities of resin.

Present single layer fiberglass substrates produced and used by applicant provide good results. However, a somewhat slower set time for the resin provides a subjective but not entirely warranted impression of a lower rigidity value.

In order to improve the perception and subjective analysis of the a single layer knitted substrate product testing was carried out with the goal to improve the time within which the substrate hardens to the optimum hardness, together with as few physical changes as possible, for example, retaining use of the same resin and knitted structure.

It has been determined that resin set time is closely related to the rate at which water ingresses into the structure of the knitted substrate, and with this in mind the tests and trials were carried out with a view towards improving water take up rate in order to set the resin faster while avoiding changes that would adversely affect the other excellent qualities of the substrate product.

As the result of testing and trials, it was ultimately found, surprisingly, that opening the needle bed gap between the top and bottom layer provided the required improvement.

Once it was determined that the needle bed gap was the determinative factor, trials to determine the most desirable needle bed gap were carried out, and results were obtained that returned rigidity results at the 4 minute time point after wetting that were 40% better than rigidity values applicable to the current knitted substrate product.

Testing included use of the commercial resin in current use and G75 glass yarn and textured glass yarn knitted on a Comez™ knitting machine.

The needle bed gap on the knitting machine was adjusted from the current 6.5 mm out to 8.0 mm. The number of wales and ends per width were set according to the tables below:

| SIZE mm | Needles/width. |
|---|---|
| 25 mm | 17 |
| 35 mm | 35 |
| 75 mm | 50 |
| 100 mm | 68 |
| 125 mm | 86 |
| 150 mm | 101 |
| 200 mm | 128 |

| Width. | BAR1 | BAR2 | BAR3 | BAR4 | BAR5 | BAR6 |
|---|---|---|---|---|---|---|
| 25 mm | 14 | 12 | 13 | 13 | 12 | 14 |
| 50 mm | 32 | 24 | 31 | 31 | 24 | 32 |
| 75 mm | 47 | 34 | 46 | 46 | 34 | 47 |
| 100 mm | 65 | 46 | 64 | 64 | 46 | 65 |
| 125 mm | 83 | 58 | 82 | 82 | 58 | 83 |
| 150 mm | 98 | 68 | 97 | 97 | 68 | 98 |
| 200 mm | 125 | 86 | 124 | 124 | 86 | 125 |

Courses per cms 7.80.
Target weight 75 mm=124.3 grms+/−0.5.
The material was knitted, using 60 rolls of each size at 30 ft lengths with 3 resin contents at 38%, 40% and 42% resin levels.

An additional 32 rolls of 25 mm, 100 mm and 150 mm wide knitted fiberglass material was prepared for transit trials and a stability study was run on the 75 mm width fabric at 25 degrees C., 40 degrees C. and 55 degrees C.

The knitted substrates were tested on an Instron Tensile Strength Tester™, using a 100 mm slab strength 3-point bend apparatus.

Prior art substrates produced with a 6 mm needle bed gap returned a 4 minute rigidity value on the Instron Tester™ of 0.6 kg/cm². In contrast, increasing the needle bed gap to 8 mm returned a 4 minute rigidity value on the Instron Tester™ of 0.9 kg/cm².

It was further determined that a needle bed gap of between 7.1 mm and 8 mm returns a 4 minute rigidity value on the Instron Tester™ of 0.9 kg/cm². Needle bed gaps greater than 8 mm return rigidity values that diminish, thus establishing that the range between 7.1 mm and 8 mm results in optimum rigidity at the 4 minute time point after wetting, with a needle bed gap of 7.3 mm most preferred.

Substrates 21 and 39 are each impregnated or coated with a reactive system which remains stable when maintained in substantially moisture-free conditions but which hardens upon exposure to sufficient moisture to form a rigid, self-supporting structure. Once removed from the knitting machine the nominal thickness of the substrate, relaxed, is 4.75 mm to 4.90 mm. The ratio of the gap to the total thickness is about 71%.

A typical formulation of the reaction system is set forth in the following table:

Typical Formulation:
Isonate 143L or polyisocyanate 50.0%
Mondur CD or Rubinate XI168 Pluracol P1010 polyol 46.6%
DC-200 Silicone defoaming agent 0.30%
Benzoyl Chloride stabilizer 0.10%
Thancat DM-70 catalyst 3.0%
Total 100%

A complete discussion of the parameters of the reactive system, the manner of production and the variables which apply are found in U.S. Pat. No. 4,411,262, referred to above. The weight of substrate 21 or 39 after being impregnated with the reactive system is preferably 3,144 g/m², with a preferred range of between 2,490 g/m to 4,534 g/m². After undergoing the curing process, the finished weight of the impregnated substrate 21 or 39 is preferably 3,168 g/m², with a preferred range of between 3,000 g/m to 4,600 g/m².

Figure 7:
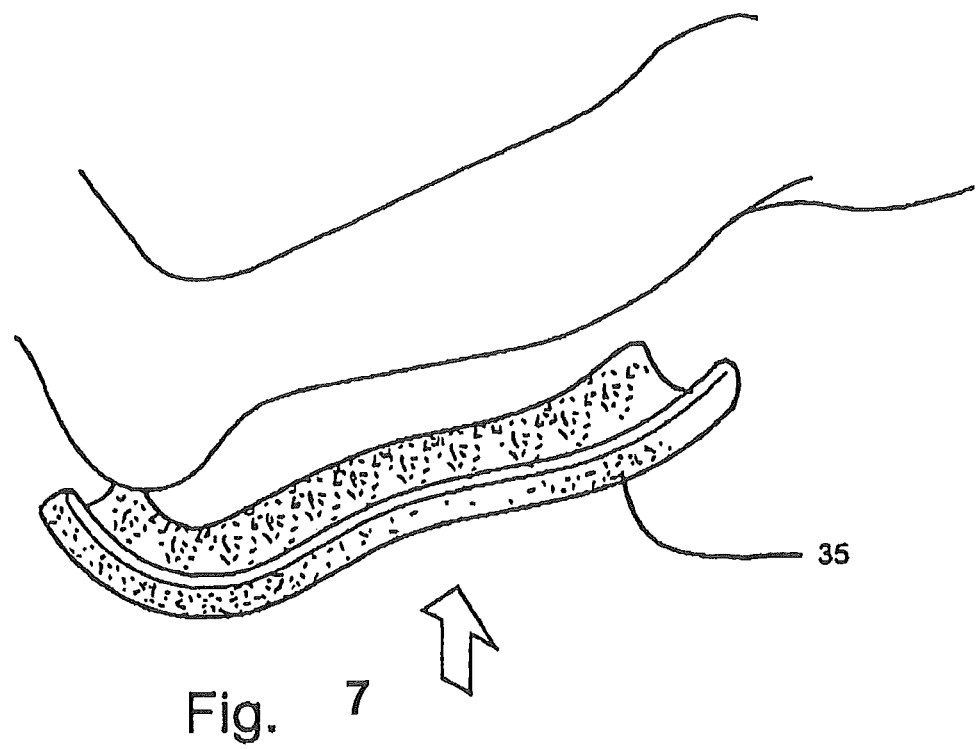
FIG. 7 illustrates a first step of applying the medical bandage material according to the present invention.
Figure 8:
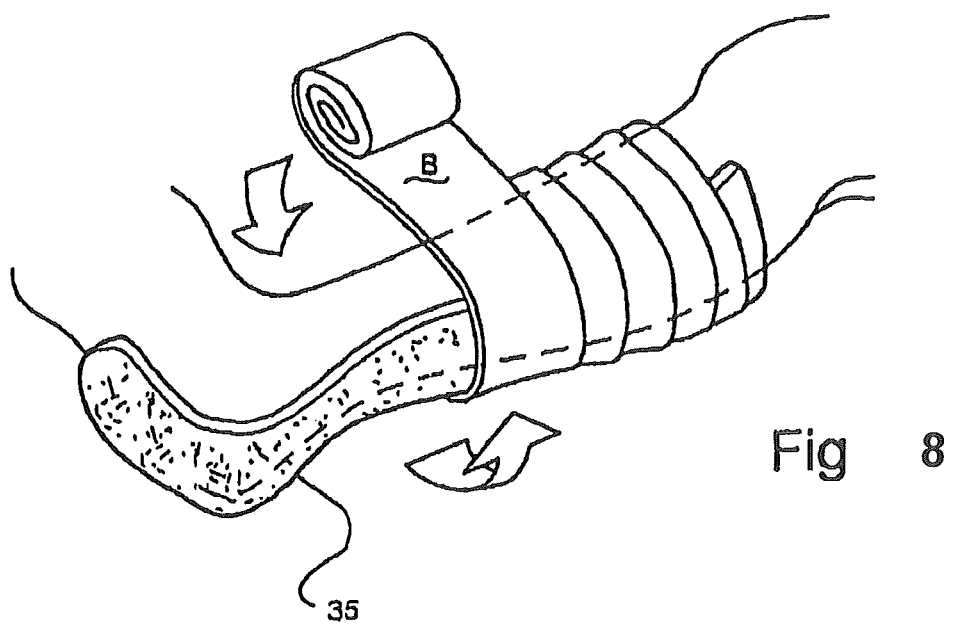
FIG. 8 illustrates a second step of applying the medical bandaging material.

Referring now to FIGS. 7 and 8, preparation and application of the medical bandaging material of the present invention is illustrated. The splint shown is commonly known as a posterior short leg splint, and is formed by molding a length of the medical bandage 35 along the calf, over the Achilles tendon and heel, and onto the foot. As is shown in FIG. 7, an appropriate length of moistened medical bandage material 35 is first formed to the shape of a body member to be immobilized. Once the bandage 35 is formed to the shape of the body member, the bandage 35 is overwrapped with a conventional elastic bandage "B", as is shown in FIG. 8.

Although the medical bandage material 35 of medical bandage product 30 is shown in FIGS. 7 and 8 in use as a posterior short leg splint, the medical bandage products 10, and 60 may be utilized in any suitable medical procedure where immobilization of one or more body members is required.

A medical bandaging product and material formed of a moisture-curable plastic material, a method for constructing such an improved medical bandage, and a method of constructing and applying an improved bandaging product is described above. Various details of the invention may be changed without departing from its scope. Furthermore; the foregoing description of the preferred embodiment of the invention and the best mode for practicing the invention are provided for the purpose of illustration only and not for the purpose of limitation—the invention being defined by the claims.

The invention claimed is:

1. A medical bandaging product comprising:
   (a) an enclosure formed of a moisture-impervious material sealable to prevent entry of moisture; and
   (b) a medical bandage material positioned in the enclosure and sealed therein against entry of moisture until use, the medical bandage material comprising:
      (i) a substrate comprising a knitted fabric layer having a major upper surface and a major lower surface, the knitted fabric layer including spaced apart edges and a plurality of interconnected knitted fabric yarns knitted such that at least one yarn extends across a gap from the major upper surface to the major lower surface along a width of the substrate in a back-and-forth pattern across the gap between the major upper surface and the major lower surface, thereby forming a single, integrated inseparable three-dimensional structure, and wherein the at least one yarn extends between non-adjacent needle positions in a back-and-forth pattern in successive courses to provide a continuous pattern on both the upper and lower major surfaces of the substrate, wherein needle bed gap spacing is between 7.1 mm and 8 mm to achieve a substrate rigidity that is greater than a substrate made from needle bed gap spacing falling outside of 7.1 mm to 8 mm, and a total thickness of the substrate is between 4.75 mm and 4.90 mm;
      (ii) a reactive system impregnated into or coated onto the substrate that remains stable when maintained in substantially moisture-free conditions and hardens upon exposure to moisture to cooperate with the three-dimensional structure to form a rigid, self-supporting structure; and
      (iii) a cushioning wrapping enclosing the substrate along its length.

2. The medical bandaging product according to claim 1, wherein the cushioning wrapping is constructed from non-woven fiber.

3. The medical bandaging product according to claim 1, wherein the cushioning wrapping is constructed of polypropylene.

4. The medical bandaging product according to claim 1, wherein the cushioning wrapping is constructed of hydrophobic fiber.

5. The medical bandaging product according to claim 1, wherein the substrate is constructed of fiberglass.

6. The medical bandaging product according to claim 1, wherein the substrate is constructed of polyester.

7. The medical bandaging product according to claim 1, wherein the knitted fabric layer is knitted on a warp knitting machine using three guide bars and three yarns.

8. The medical bandaging product according to claim 7, wherein a first yarn is threaded on a front guide bar and has back-and-forth movement to non-adjacent needles in successive courses, and second and third yarns are threaded on the respective middle and back guide bars and have similar movements.

9. The medical bandaging product according to claim 7, wherein first, second and third yarns are knitted on respective front, middle and back guide bars continuously.

10. The medical bandaging product according to claim 1, wherein the needle bed gap spacing is 7.3 mm.

11. The medical bandaging product according to claim 1, wherein a ratio of the needle bed gap spacing to the total thickness is 71%.

12. The medical bandaging product according to claim 1, wherein a weight of the substrate after being impregnated with the reactive system is between 2,490 g/m$^2$ and 4,534 g/m$^2$.

13. The medical bandaging product according to claim 1, wherein a finished weight of the impregnated substrate is between 3,000 g/m$^2$ to 4,600 g/m$^2$.

14. A substrate comprising:
- a knitted fabric layer having a major upper surface and a major lower surface, the knitted fabric layer including spaced apart edges and a plurality of interconnected knitted fabric yarns knitted such that at least one yarn extends across a gap from the major upper surface to the major lower surface along a width of the substrate in a back-and-forth pattern across the gap between the major upper surface and the major lower surface, thereby forming a single, integrated inseparable three-dimensional structure;
- wherein the at least one yarn extends between non-adjacent needle positions in a back-and-forth pattern in successive courses to provide a continuous pattern on both the upper and lower major surfaces of the substrate;
- wherein needle bed gap spacing is between 7.1 mm and 8 mm to achieve a substrate rigidity that is greater than a substrate made from needle bed gap spacing falling outside of 7.1 mm to 8 mm; and
- a total thickness of the substrate is between 4.75 mm and 4.90 mm.

* * * * *